(12) United States Patent
Popovic et al.

(10) Patent No.: US 8,292,904 B2
(45) Date of Patent: Oct. 23, 2012

(54) DEVICE, CLIP, ENDOSCOPE AND METHOD FOR THE INTRALUMINAL TREATMENT OF TISSUE, E.G. HEMORRHOIDS

(75) Inventors: Drago Popovic, Sunrise Beach (AU); Brian J. Thompson, Cincinnati, OH (US); Alessandro Pastorelli, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 704 days.

(21) Appl. No.: 12/278,401

(22) PCT Filed: Jul. 26, 2006

(86) PCT No.: PCT/EP2006/007355
§ 371 (c)(1),
(2), (4) Date: Apr. 13, 2009

(87) PCT Pub. No.: WO2007/093198
PCT Pub. Date: Aug. 23, 2007

(65) Prior Publication Data
US 2010/0023023 A1    Jan. 28, 2010

(30) Foreign Application Priority Data

Feb. 15, 2006 (IT) .............................. MI2006A0281
Mar. 21, 2006 (IT) .............................. MI2006A0509

(51) Int. Cl.
*A61B 17/10* (2006.01)
(52) U.S. Cl. ...................................................... 606/142
(58) Field of Classification Search ................ 227/175.1; 606/139–143
See application file for complete search history.

(56) References Cited

U.S. PATENT DOCUMENTS

| 2,922,415 | A | * | 1/1960 | Campagna | 600/184 |
|---|---|---|---|---|---|
| 4,513,746 | A | | 4/1985 | Aranyi et al. | |
| 4,566,620 | A | | 1/1986 | Green et al. | |
| 4,834,067 | A | * | 5/1989 | Block | 600/184 |
| 5,156,315 | A | | 10/1992 | Green et al. | |
| 5,403,326 | A | * | 4/1995 | Harrison et al. | 606/139 |
| 6,083,241 | A | * | 7/2000 | Longo et al. | 606/219 |
| 6,099,537 | A | * | 8/2000 | Sugai et al. | 606/143 |
| 6,773,443 | B2 | * | 8/2004 | Truwit et al. | 606/169 |
| 7,118,528 | B1 | * | 10/2006 | Piskun | 600/105 |
| 2002/0062130 | A1 | | 5/2002 | Jugenheimer et al. | |
| 2002/0077646 | A1 | * | 6/2002 | Truwit et al. | 606/170 |

(Continued)

FOREIGN PATENT DOCUMENTS

CN      1636522 A      7/2005

(Continued)

OTHER PUBLICATIONS

EPO Search Report dated Jan. 4, 2007 for corresponding patent application, European Patent Application No. PCT/EP2006/007355.

*Primary Examiner* — Melanie Tyson
*Assistant Examiner* — Son Dang

(57) ABSTRACT

A device for the intraluminal treatment of tissue comprises a handle, a shaft which extends from the handle and a head arranged at the distal end of the shaft, wherein the head comprises at least one jaw, movable between an open position, wherein it defines a window for the insertion of the tissue and surrounding tissue, and a closed position, and wherein the shaft extends between the handle and head in a curvilinear longitudinal direction.

7 Claims, 18 Drawing Sheets

U.S. PATENT DOCUMENTS

| | | |
|---|---|---|
| 2004/0059359 A1 | 3/2004 | Wilson, Jr. |
| 2004/0094597 A1* | 5/2004 | Whitman et al. .......... 227/180.1 |
| 2004/0222268 A1* | 11/2004 | Bilotti et al. ............... 227/180.1 |

FOREIGN PATENT DOCUMENTS

| | | |
|---|---|---|
| EP | 0136949 A | 4/1985 |
| EP | 1600108 B1 | 12/2009 |
| JP | 6-165786 A | 6/1994 |
| WO | WO 01/91646 A | 12/2001 |
| WO | WO 2004/112583 A2 | 12/2004 |
| WO | WO 2006/015222 A2 | 2/2006 |

\* cited by examiner

DEVICE, CLIP, ENDOSCOPE AND METHOD FOR THE INTRALUMINAL TREATMENT OF TISSUE, E.G. HEMORRHOIDS

The present invention relates to a device, clip, anoscope and method for the intraluminal treatment of body tissue, e.g. for the transanal treatment of hemorrhoids or for intraluminal or endoscopic treatments of body tissue different from hemorrhoids.

Also object of the present invention is an endoscope, e.g. an anoscope for the treatment of lower rectum pathologies, for example for the minimally-invasive surgical treatment of hemorrhoids.

Apart from endoscopic o intraluminal treatments of body tissue which is different from hemorrhoids, such aspects of the invention are in particular correlated with the realization of a minimally-invasive surgical treatment for the treatment of so-called "internal" hemorrhoids, i.e. above the anorectal junction (dentate line).

One of the known methods of surgical treatment of hemorrhoids is the method of hemorrhoid ligation by means of a rubber elastic band wherein each hemorrhoid is inserted in a hollow cylindrical device, and a rubber elastic band is positioned on the hemorrhoid. The compression exerted by the rubber elastic band subsequently leads to the necrosis and thus the shedding of the tissue.

Such method, together with the devices employed, has several drawbacks. In particular, the rubber elastic band cannot be deeply positioned, at the root of the hemorrhoid, and due to its elastic nature it tends to conform to the tissue, with the consequence that the treatment cannot be radical.

An additional method is known, known as PPH, along with a corresponding application device of such method. The device is substantially composed of a circular stapler adapted to be inserted into the anal canal and stable and cut a ring of tissue which comprises the hemorrhoids. In this case, the cut affects the entire section of the anal canal and produces a rather large wound.

The problem underlying the present invention is that of proposing a device, clip and method for the intraluminal treatment of body tissue, e.g. for the transanal treatment of hemorrhoids or for intraluminal or endoscopic treatments of body tissue different from hemorrhoids which has structural and functional characteristics such to overcome the aforementioned drawbacks cited with reference to the prior art.

Such problem is solved by means of a device for the intraluminal treatment of body tissue, e.g. for the transanal treatment of hemorrhoids or for intraluminal or endoscopic treatments of body tissue different from hemorrhoids, a clip for the intraluminal treatment of body tissue, e.g. for the transanal treatment of hemorrhoids or for intraluminal or endoscopic treatments of body tissue different from hemorrhoids and a method for the intraluminal treatment of body tissue, e.g. for the transanal treatment of hemorrhoids or for intraluminal or endoscopic treatments of body tissue different from hemorrhoids.

A further problem underlying the present invention is that of proposing an endoscope, e.g an anoscope of easy and effective use, in particular adapted for use in a method for the intraluminal treatment of body tissue, e.g. for the transanal treatment of hemorrhoids or for intraluminal or endoscopic treatments of body tissue different from hemorrhoids, for example together with the abovementioned devices.

Such problem is solved by means of an endoscope for the treatment pathologies of natural ducts of the human or animal body, e.g. an anoscope for lower rectum pathologies, for example for the minimally-invasive surgical treatment of hemorrhoids.

Further characteristics and advantages of the device, clip, endoscope or anoscope and method according to the invention will be clearer from the below description of preferred embodiments (referred to applications in the treatment of hemorrhoids, but not intended to be limited to such applications), given as indicative and not limiting with reference to the attached figures, wherein.

Figure 1:
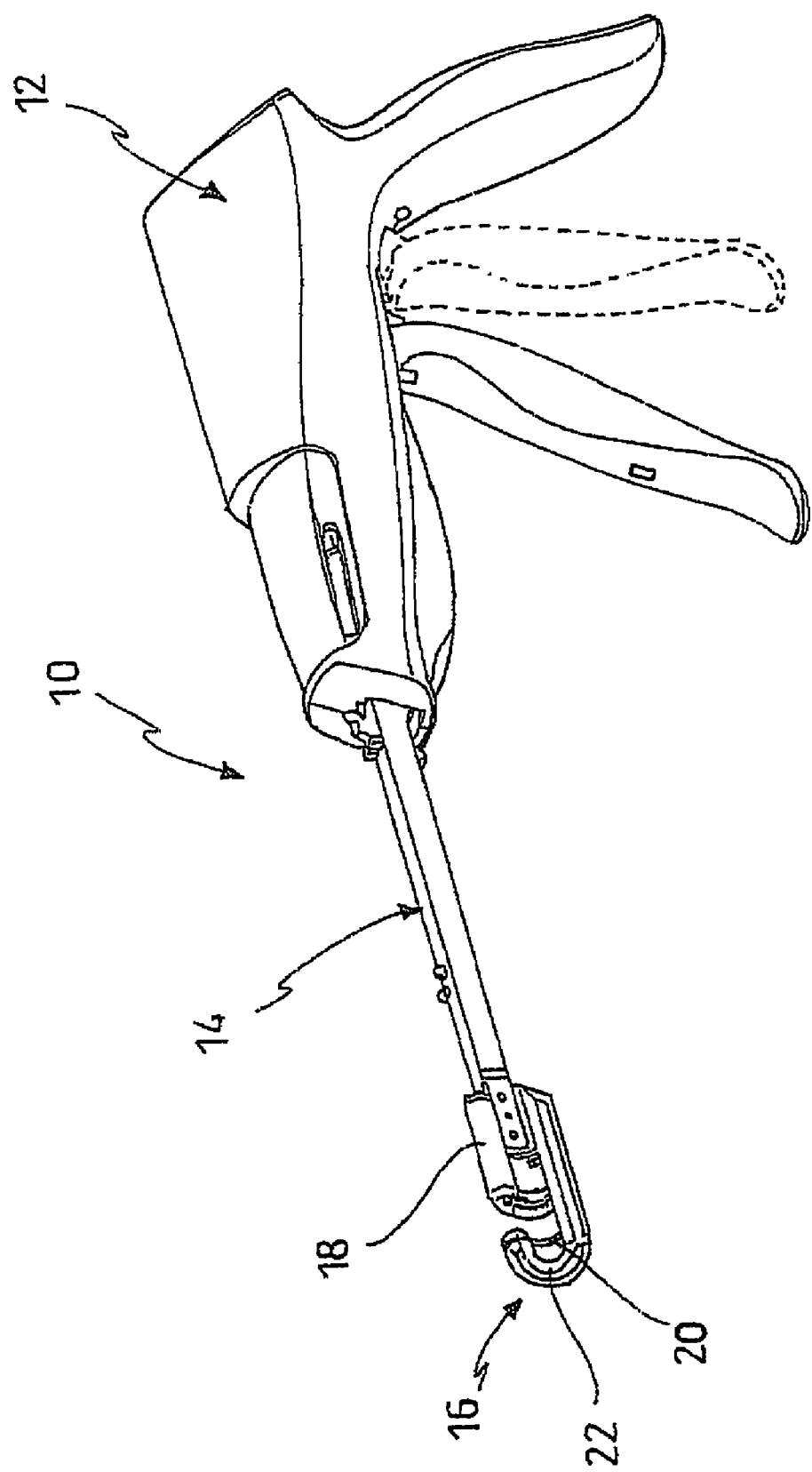
FIG. 1 illustrates a perspective view of an embodiment of a device for the transanal treatment of hemorrhoids.
Figure 2:
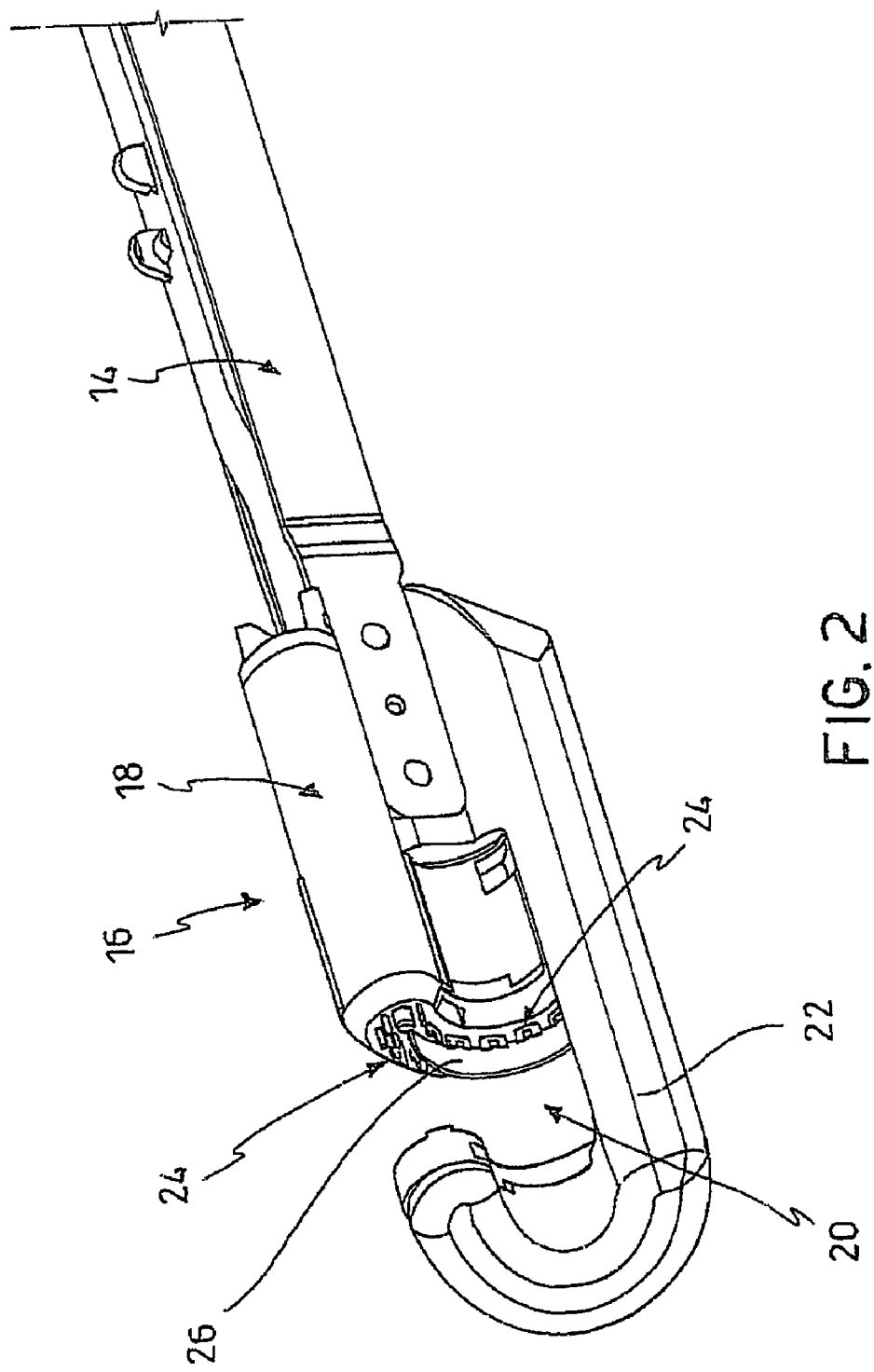
FIG. 2 illustrates an enlarged detail of the device of FIG. 1.
Figure 3:
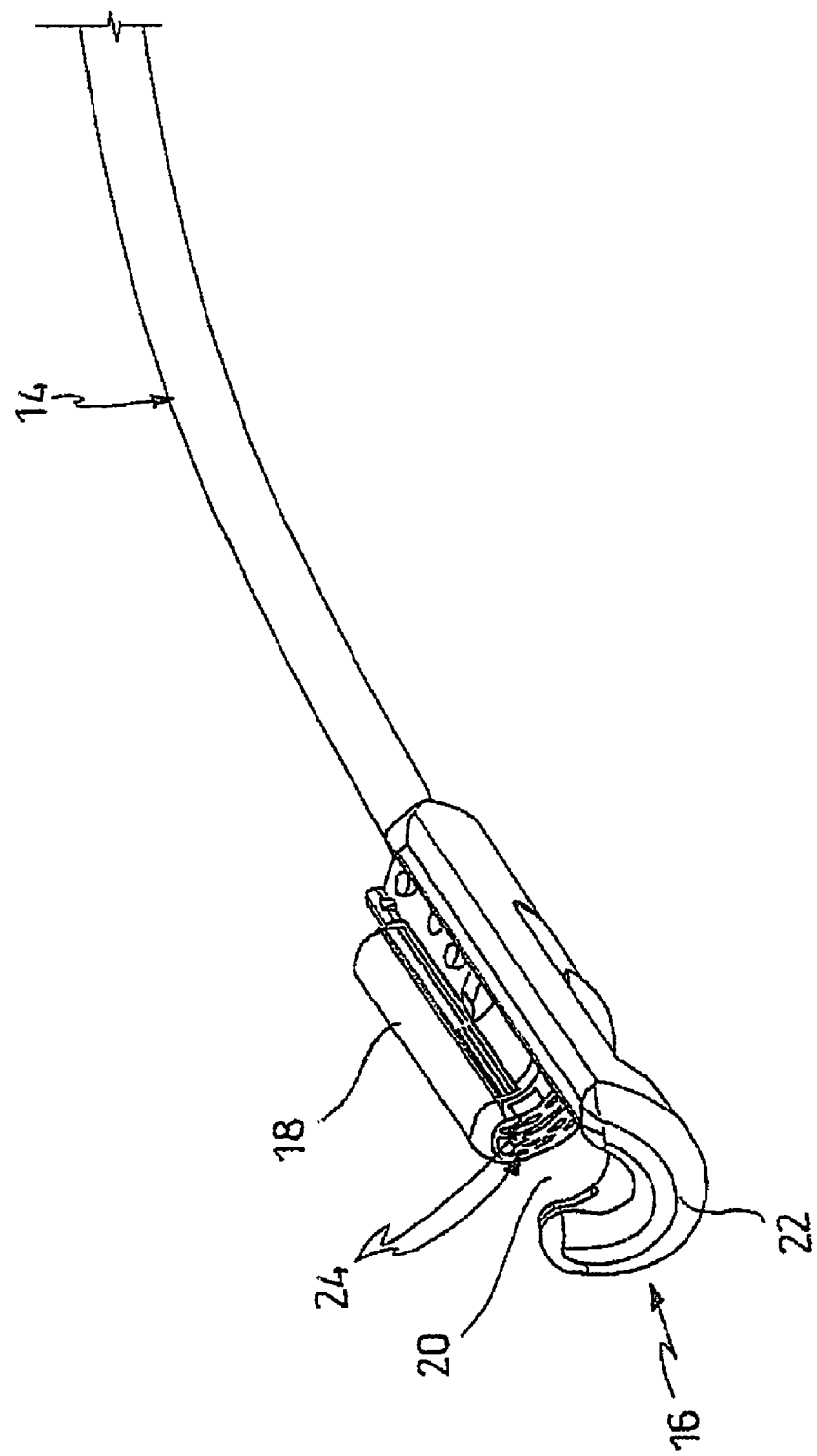
FIG. 3 illustrates an enlarged detail of a possible embodiment of the device of FIG. 1.
Figure 4:
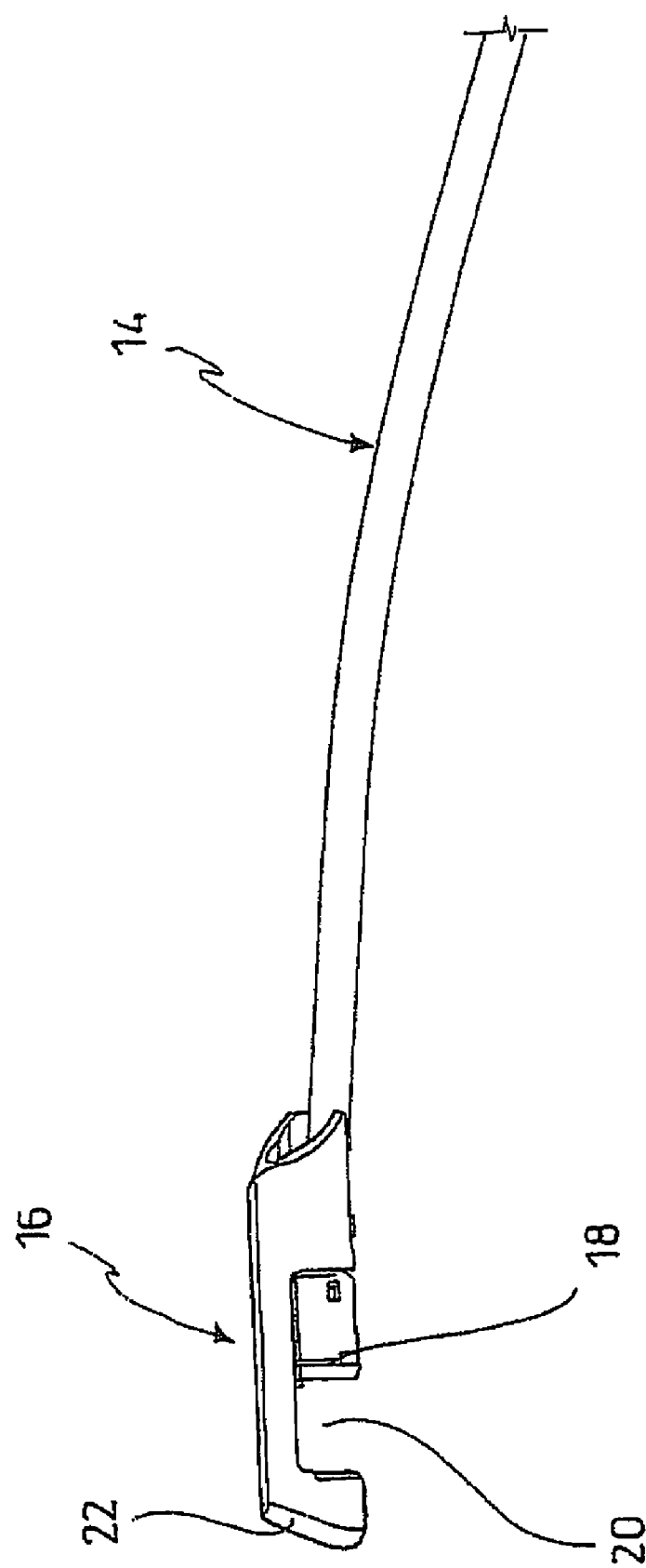
FIG. 4 illustrates the detail of FIG. 3 from a different angle.
Figure 5:
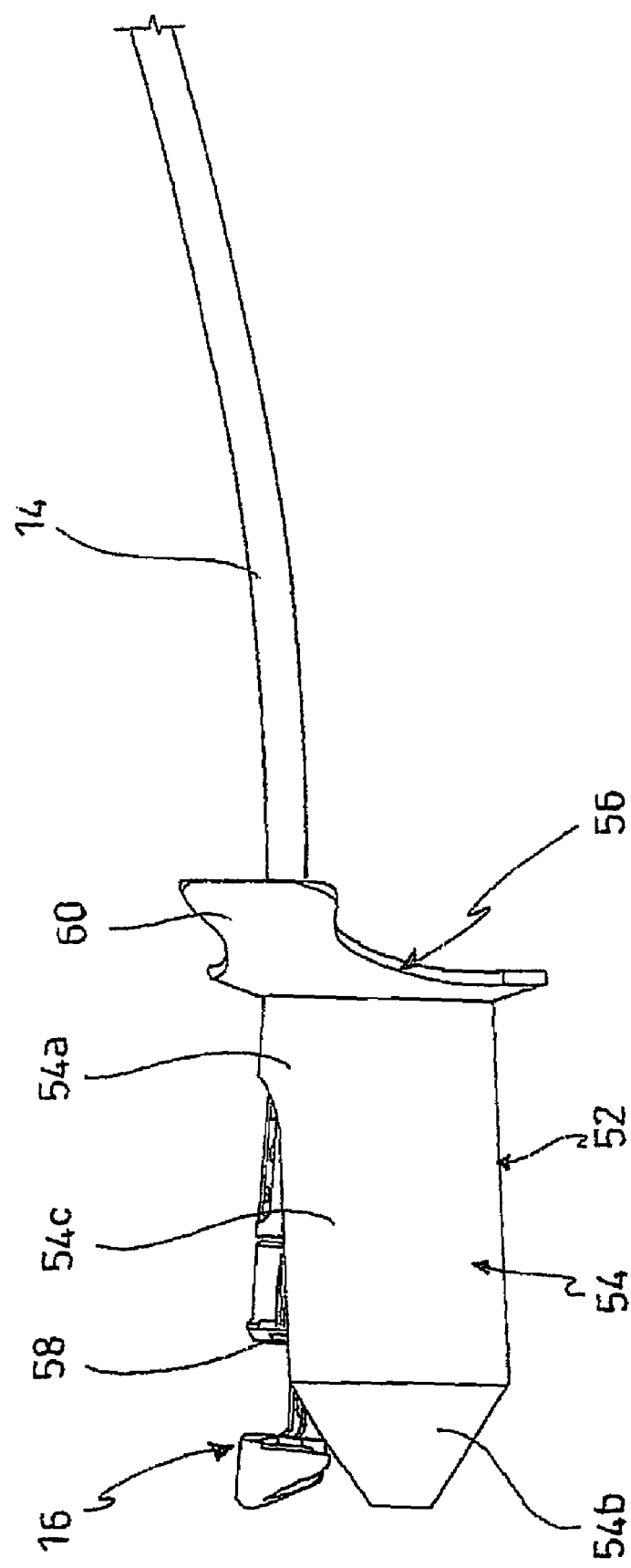
FIG. 5 illustrates the detail of FIG. 3 from a different angle and associated with an anoscope according to the present invention.
Figure 6:
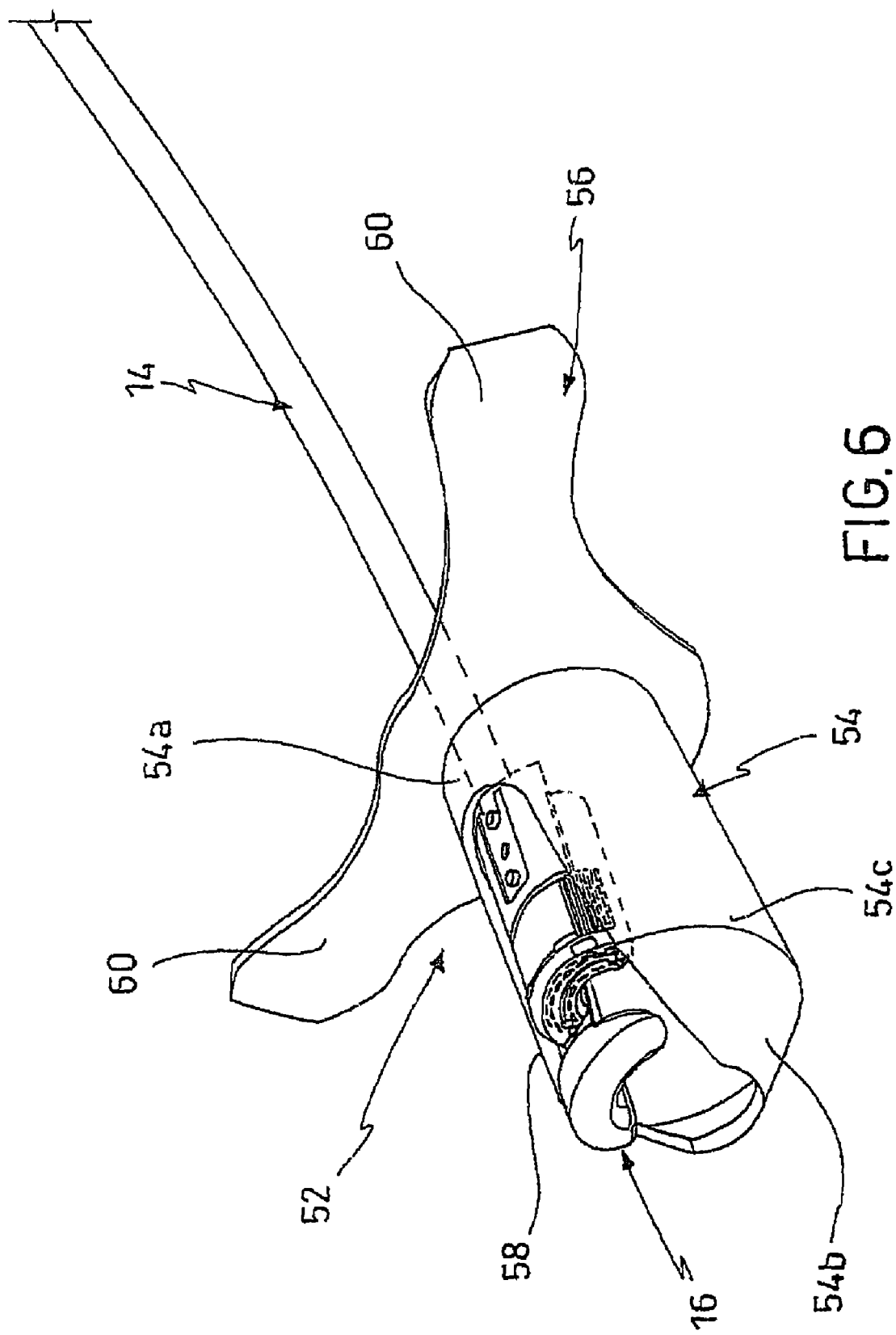
FIG. 6 illustrates the detail and anoscope of FIG. 5 from a different angle.
Figure 7:
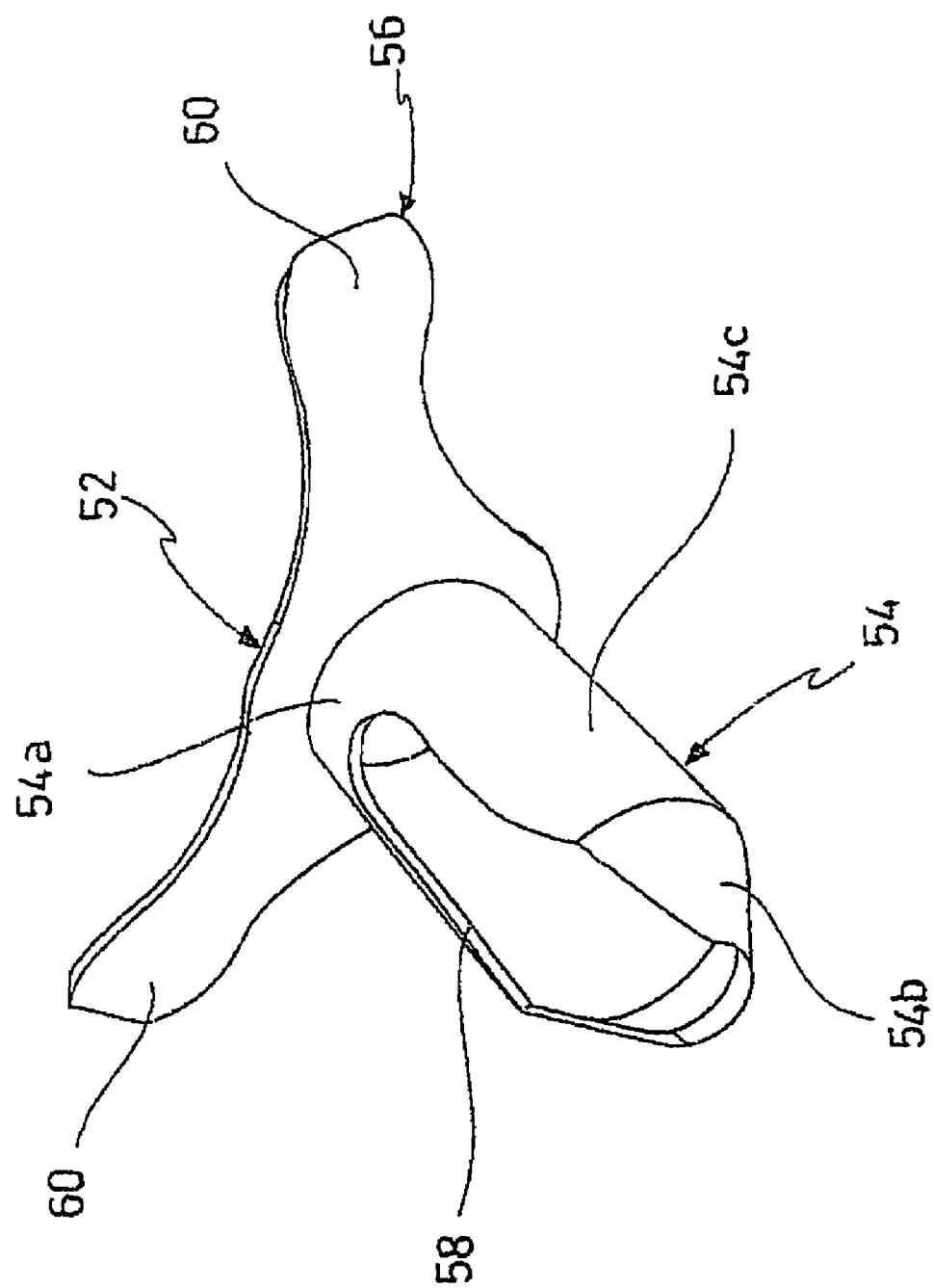
FIG. 7 illustrates a perspective view of an anoscope according to the present invention.
Figure 8:
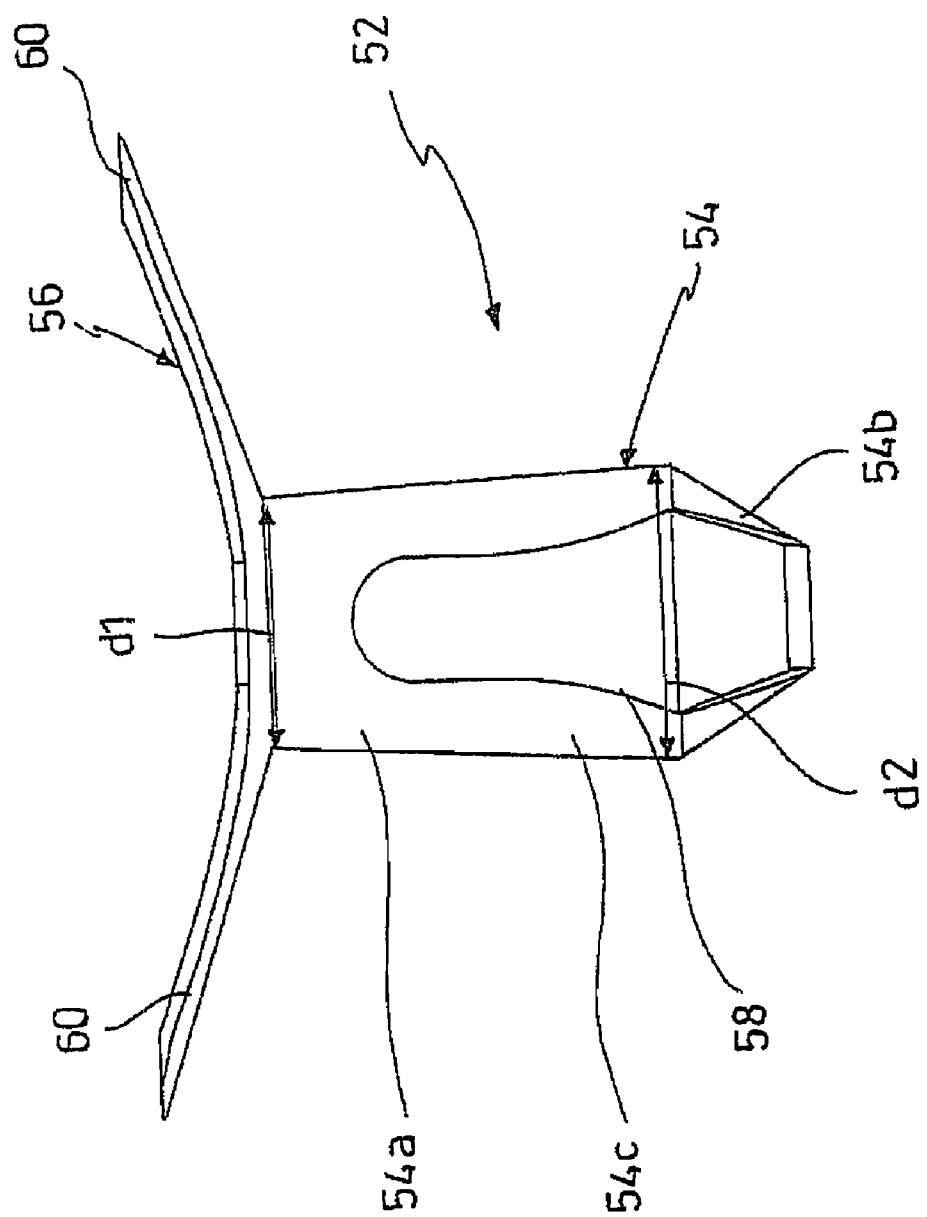
FIG. 8 illustrates a side view of the anoscope of FIG. 7.
Figure 9:
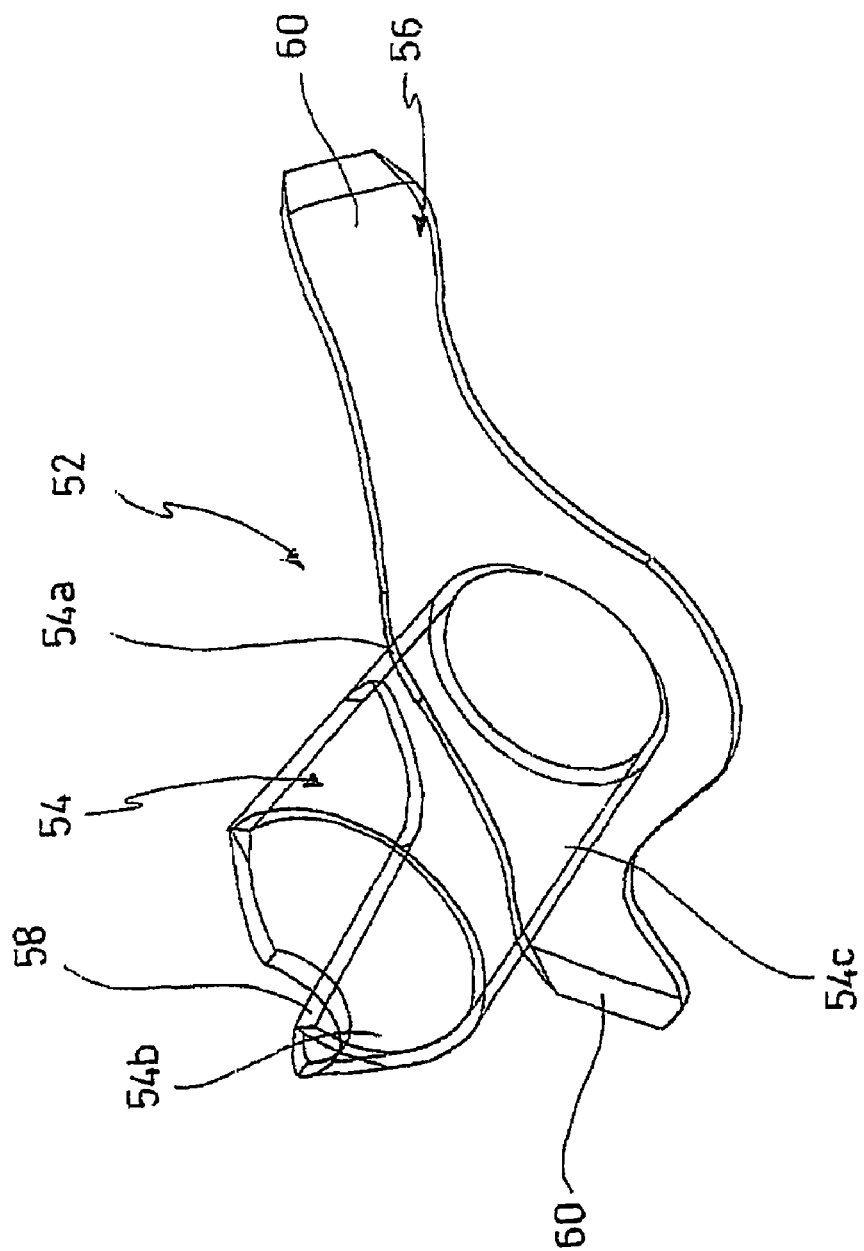
FIG. 9 illustrates a perspective view of the anoscope of FIG. 7.
Figure 10:
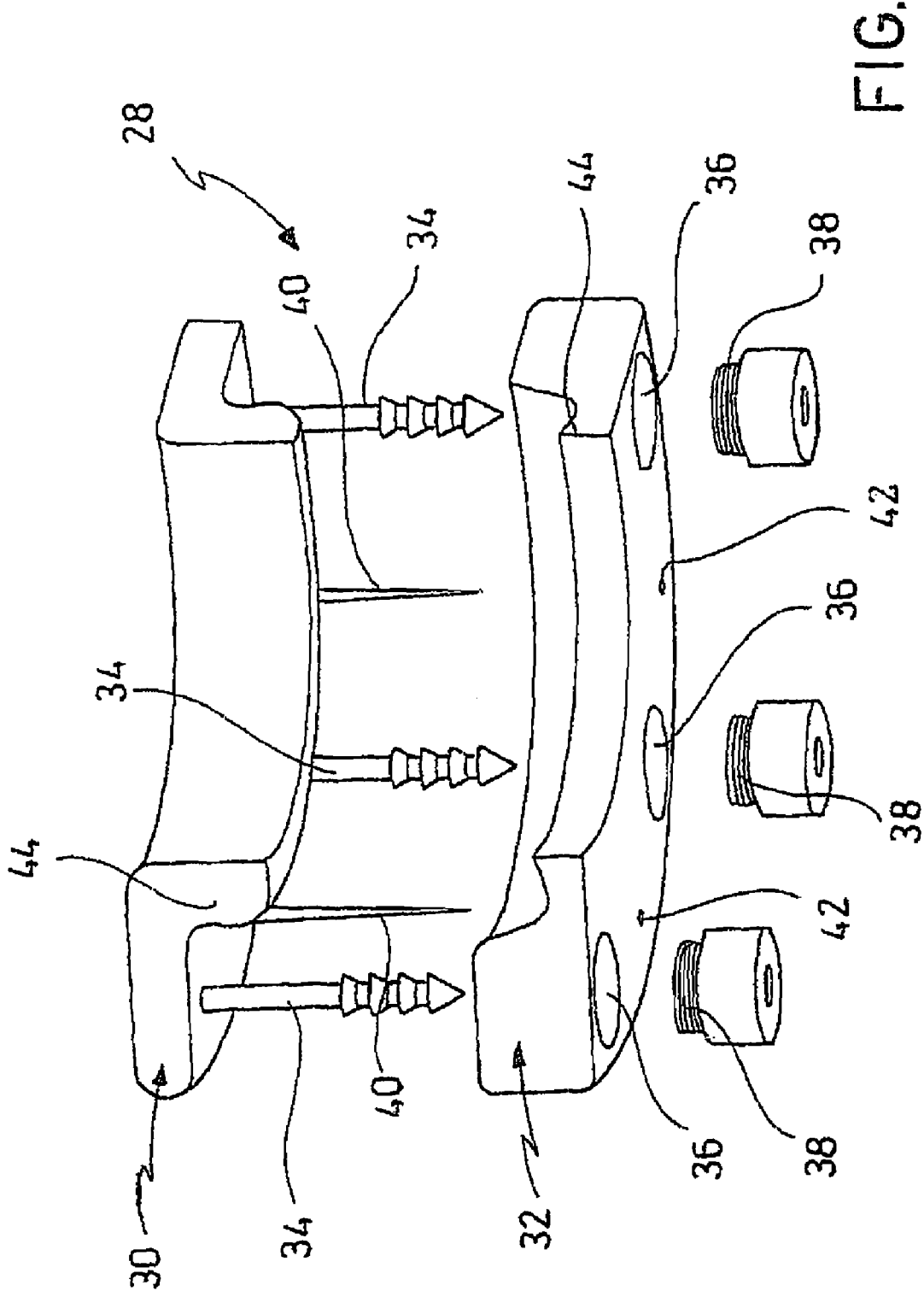
FIG. 10 illustrates a perspective and separated parts view of a possible embodiment of a clip according to the present invention.
Figure 11:
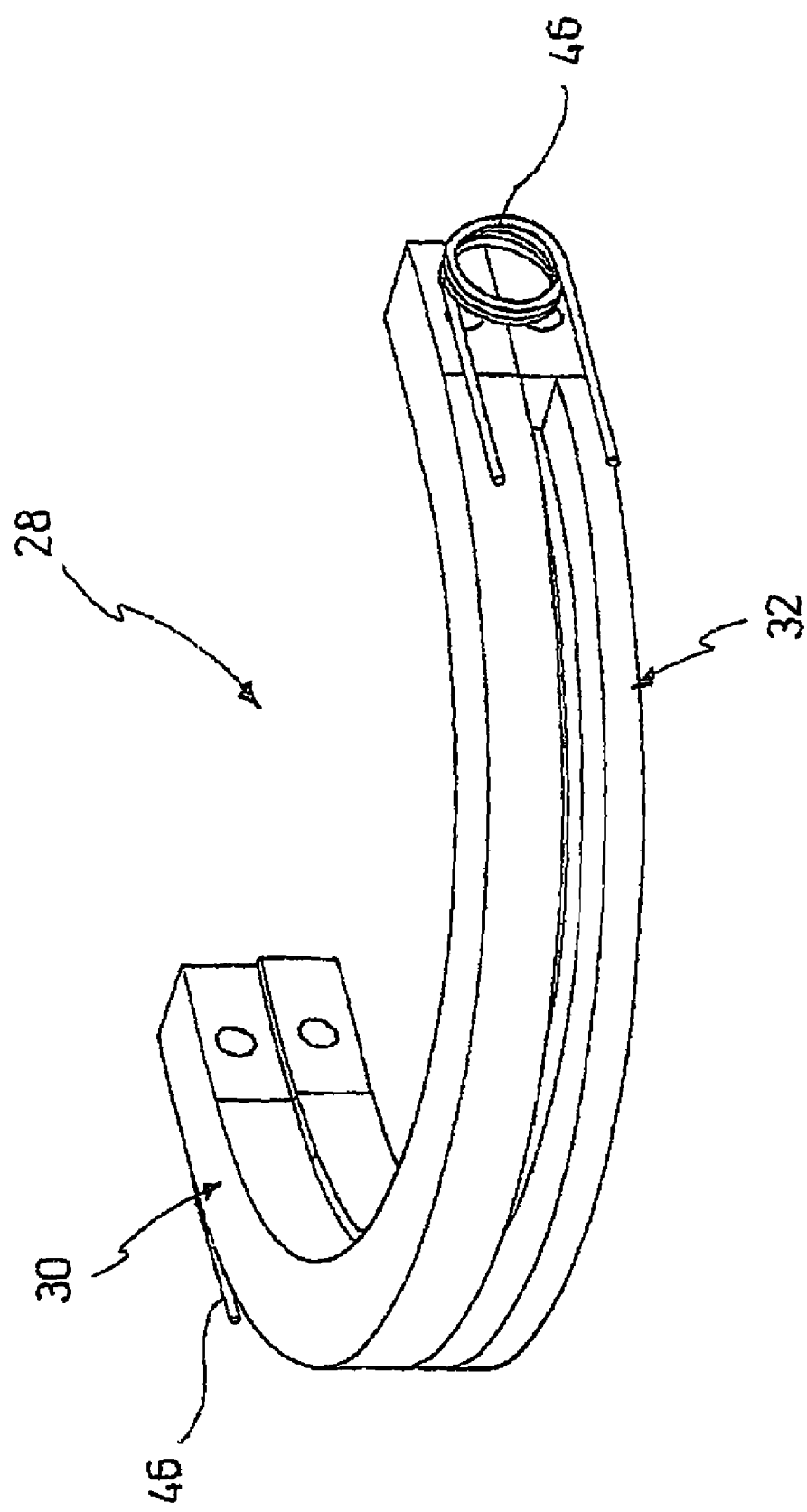
FIG. 11 illustrates a perspective view of a possible embodiment of a clip according to the present invention in a first condition of use.
Figure 12:
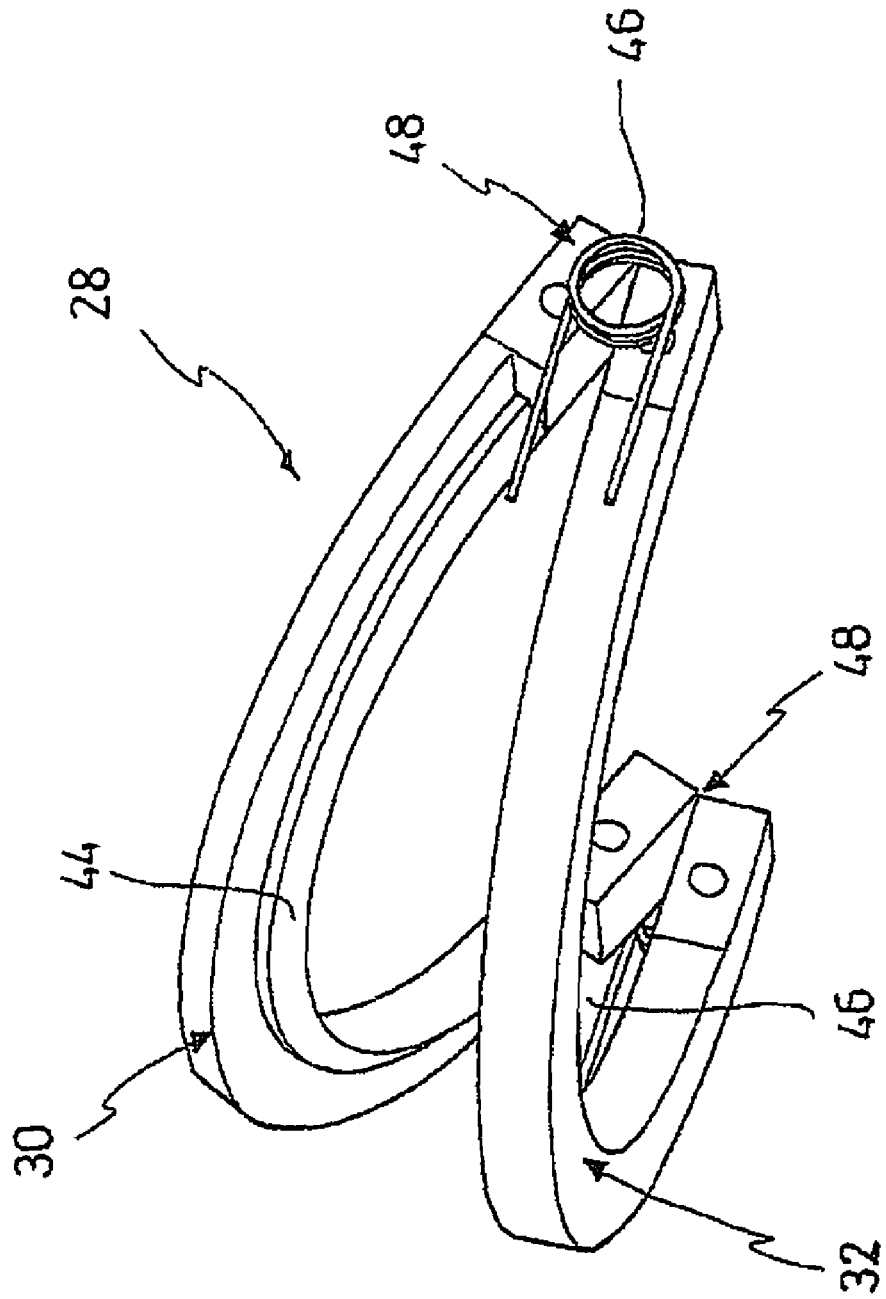
FIG. 12 illustrates the clip of FIG. 11 in a second condition of use.
Figure 13:
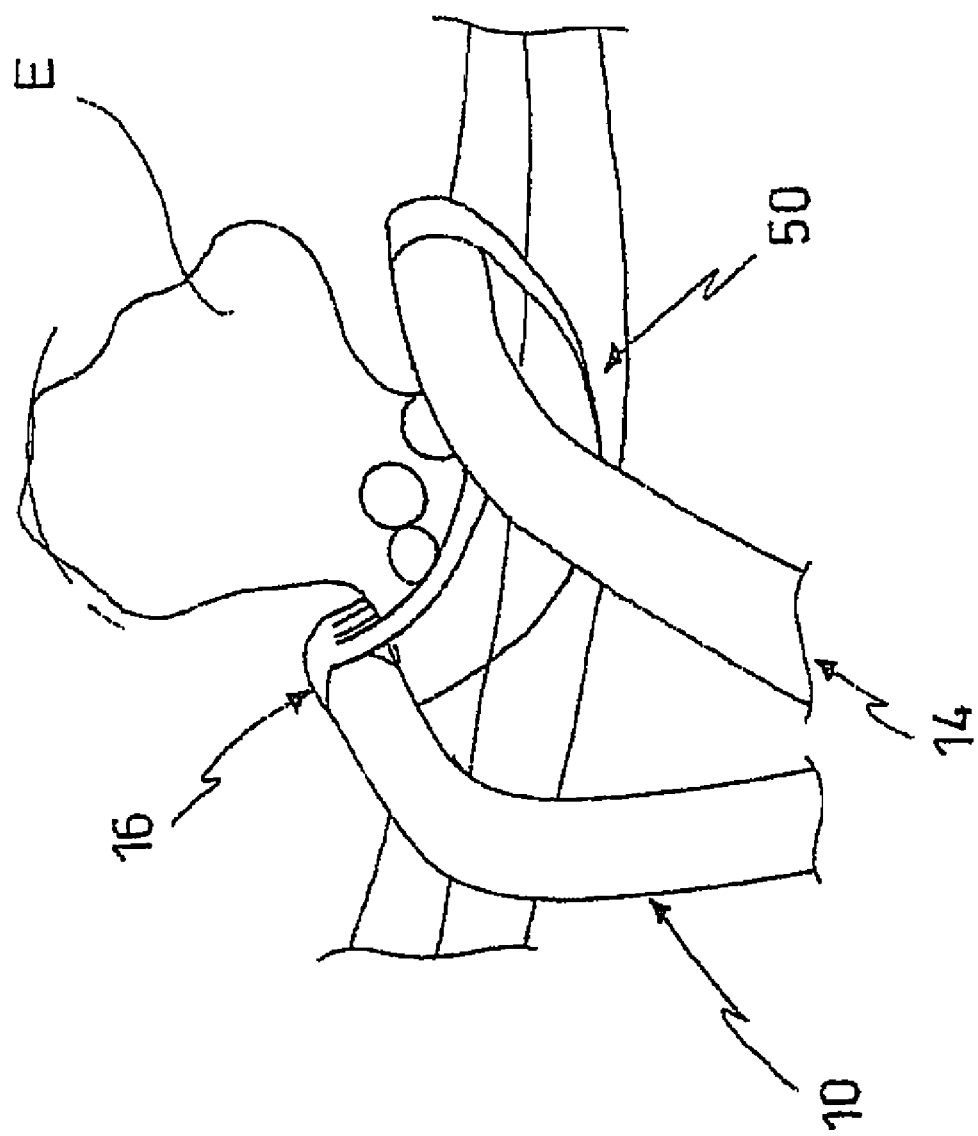
FIG. 13 illustrates an enlarged view of a possible embodiment of a detail of the device of the present invention.
Figure 14:
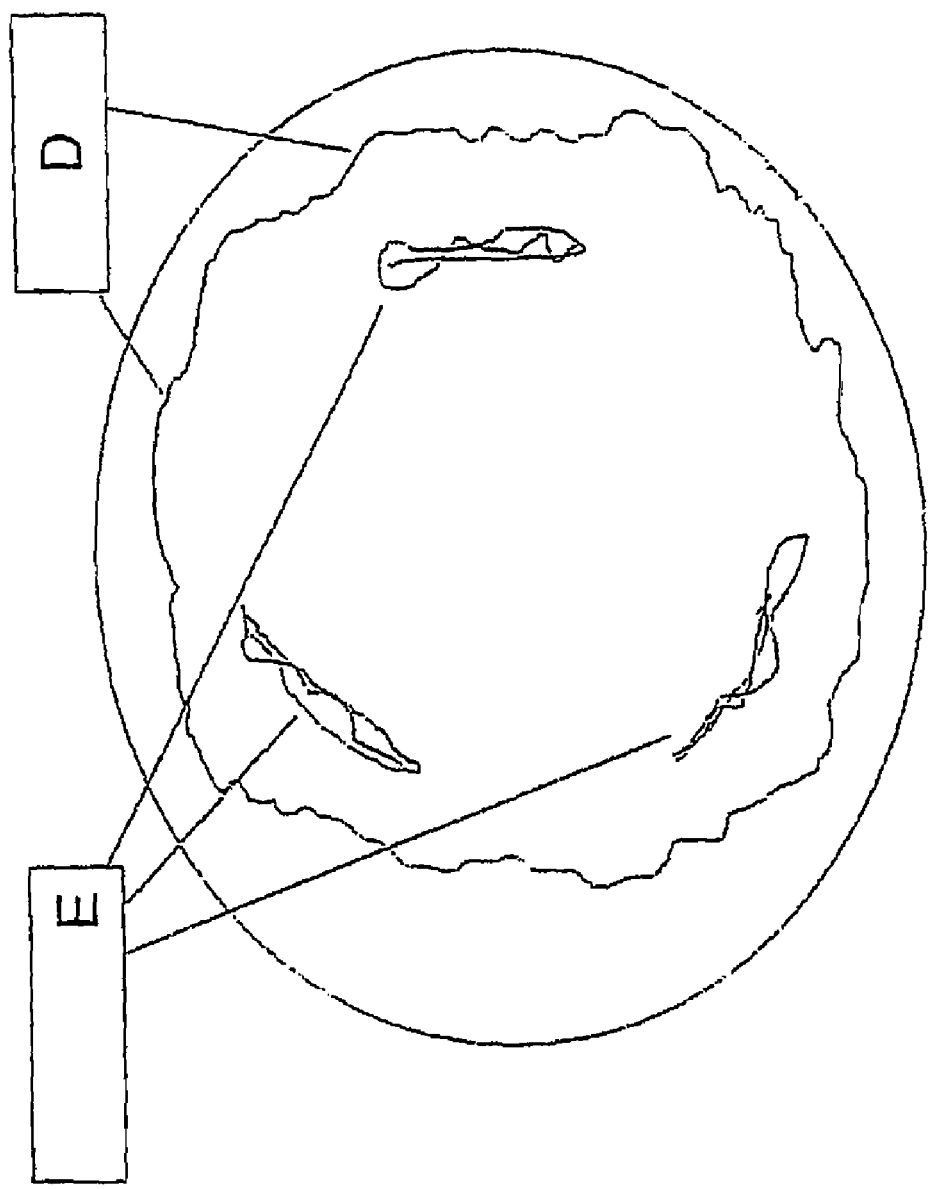
FIG. 14 illustrates a cross section of the anal canal.
Figure 15:
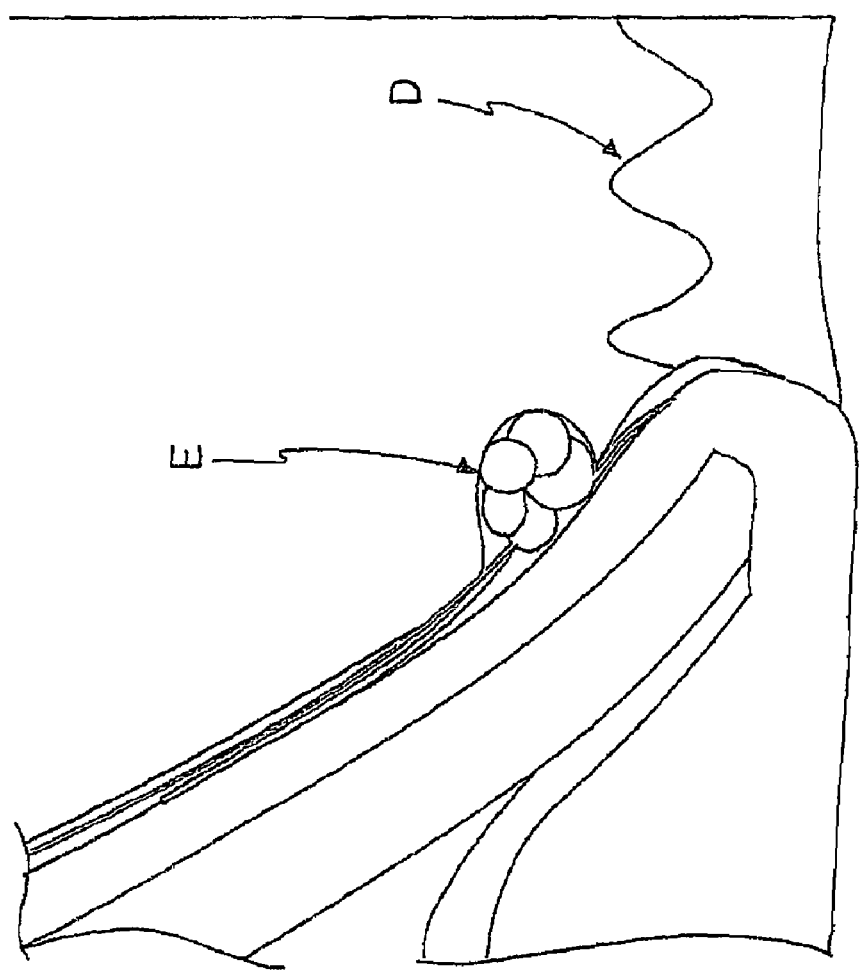
FIG. 15 illustrates a longitudinal section of the anal canal.
Figure 16:
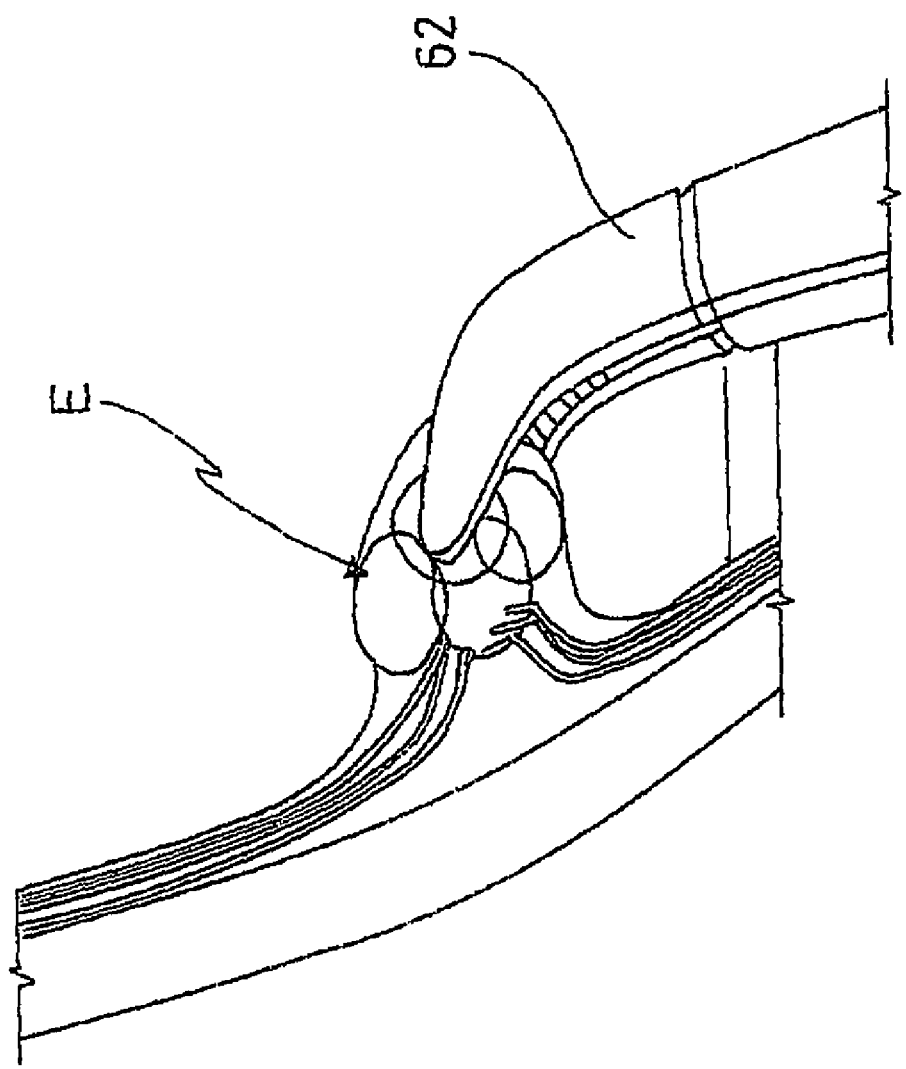
Figure 17:
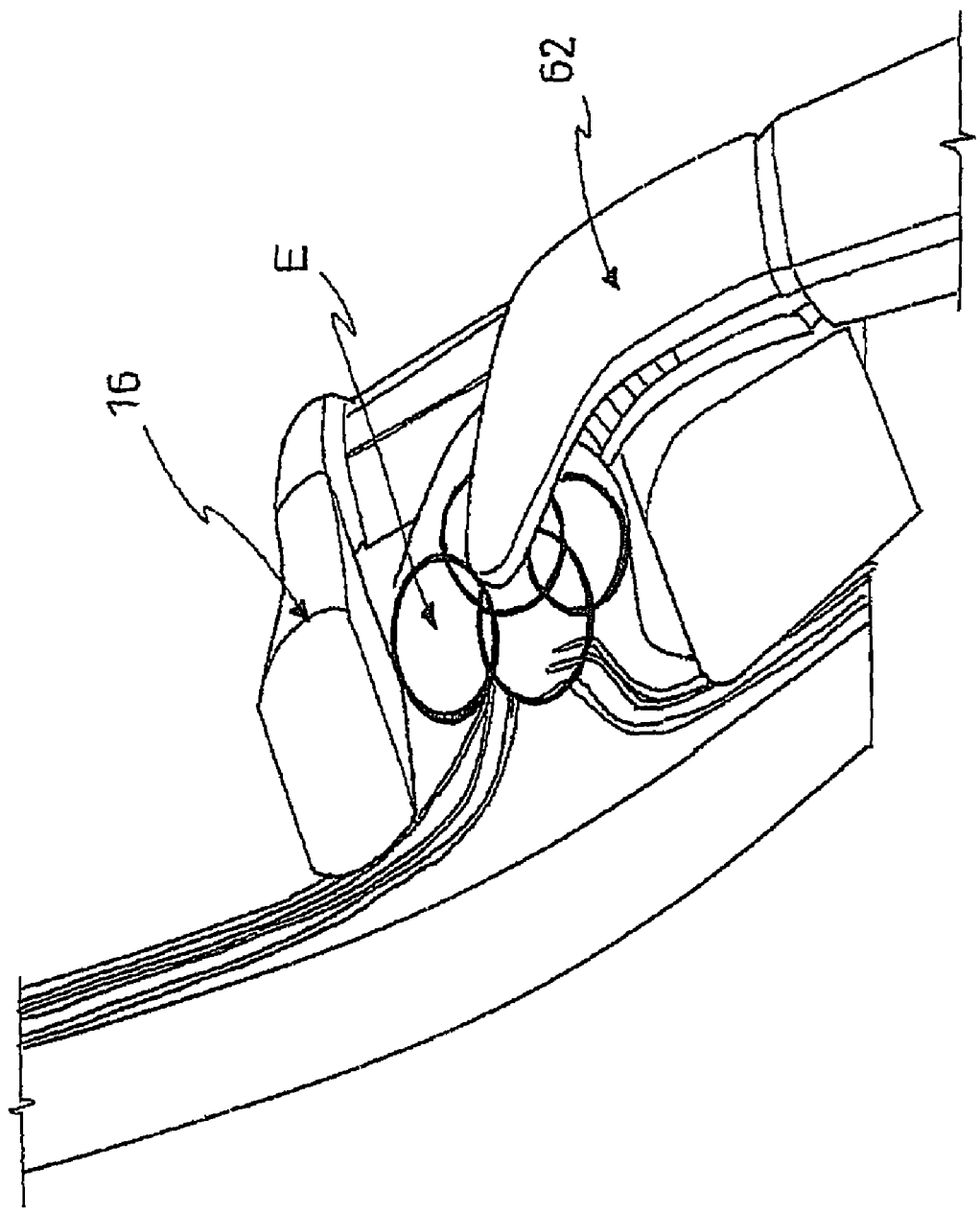
Figure 18:
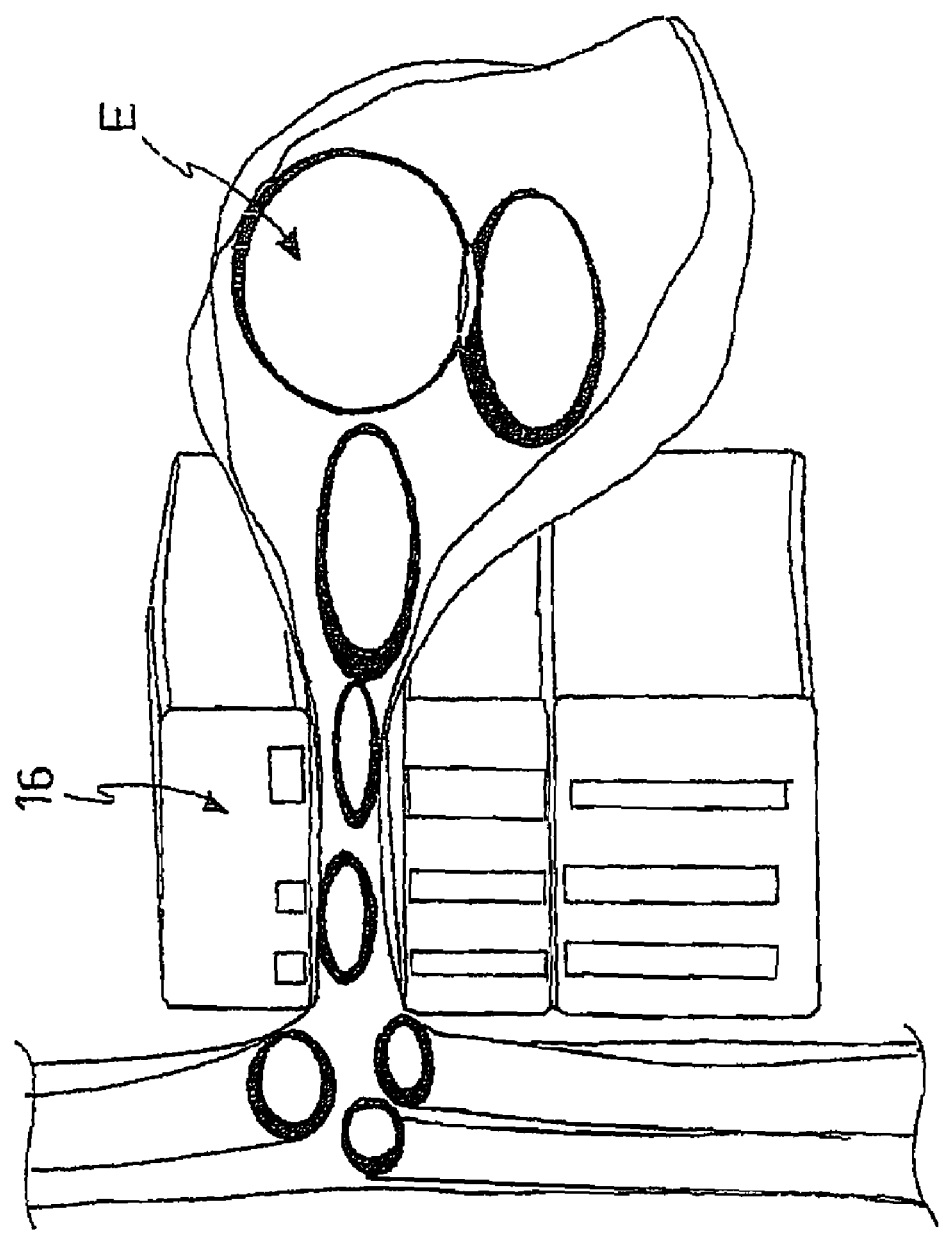

FIGS. 16-18 respectively illustrate a detail of FIG. 15 in a subsequent step of the method according to the invention.

With reference to the abovementioned figures, a device for the transanal treatment of hemorrhoids is indicated in its entirety with 10.

Such device comprises a handle 12 and a shaft 14 which extends from the handle. A head 16 is arranged at the distal end of the shaft, i.e. at the end away from the surgeon or operator who holds and operates the device.

The head 16 comprises at least one jaw 18, movable between an open position, wherein it defines a window 20 for the insertion of the hemorrhoid and surrounding tissue, and a closed position.

According to the preferred embodiment illustrated in the drawings, the window 20 is open laterally, in the open position of the jaw 18.

A jaw opposing the movable jaw is indicated with 22. In the illustrated example, the opposing jaw is fixed and distal with respect to the movable jaw. In accordance with different embodiments, it is possible to foresee that both jaws are movable or else that the position of the movable jaw and opposing jaw is reversed, foreseeing the movable jaw in distal position with respect to the opposing jaw.

Advantageously, the shaft 14 may extend between the handle and the head in a curvilinear longitudinal direction.

Advantageously, the head, in particular the two jaws, has a curvilinear conformation.

In accordance with one embodiment of the invention, the device 10 is a linear or slightly curvilinear stapler. The head comprises at least one row 24 of clipping elements or staples which may be clasped to the hemorrhoid and the surrounding tissue in order to clot the tissue and obtain hemostasis. Preferably the staples are clasped to the hemmorrhoid after the head movement from the open to the closed position. In particular the handle comprises first means for closing the jaws and second means for clasping the staples to the tissue. In a different embodiment, the staples are clasped to the tissue by means of the head movement from the open position to the closed position.

Preferably, at least two rows 24 of clipping elements are foreseen, arranged substantially parallel to each other. Possibly, there may be foreseen more than two rows of clipping elements.

In the illustrated example, the clipping elements are arranged in the movable jaw 18. The opposing jaw compels the clipping elements to bend and cling to the tissue, in passing from the head's open position to the closed position.

In accordance with a possible embodiment, a knife 26 is further foreseen adjacent to at least one row 24 of clipping elements, for cutting the hemorrhoid and the surrounding tissue. Preferably the knife is positioned adjacent to a row of staples suitable for being clasped to the tissue at the side of the anal duct. The knife is suitable for cutting the tissue at the side of the hemorrhoid, without any row of staples on the hemorrhoid itself. Therefore the tissue of the anal duct is clotted obtaining hemostasis by means of the staples. In a different embodiment, in the case of two or more rows 24 of clipping elements, the knife may be arranged between the two rows so that a first line of stapling belongs to the tissue which will be removed and a second line of stapling belongs to the tissue of the anal canal.

In accordance with a different embodiment, the device 10 comprises a head adapted to receive at least one clip 28 and to tighten it on the hemorrhoid through the window. In other words, the head, which may be curvilinear, does not comprise multiple clipping elements or staples but is realized so to house one clip between the jaws.

Possibly, the head moreover comprises a knife 26 for cutting the hemorrhoid and the surrounding tissue compressed by the clip.

The clip 28 for the transanal treatment of hemorrhoids comprises two complementary elements 30, 32 adapted to be mutually locked in at least one compression position of the hemorrhoid and adjacent tissue. Preferably, the clip 28 comprises two complementary curvilinear elements 30, 32 adapted to be housed in a head of a device for the transanal treatment of the hemorrhoids as previously described.

In accordance with a first embodiment, the clip 28 comprises a first element 30 provided with at least one locking pin 34 adapted to be inserted in a corresponding seat 36 of the second element 32. The seat 36 comprises at least one elastic element 38 and the locking pin 34 is shaped so to be snap-locked inside the seat 36.

Possibly, the first and second element 30, 32 respectively comprise guides 40 and sliding seats 42 for the mutual positioning of the two elements 28, 30.

Advantageously, the complementary elements 30, 32 comprise mutual compression portions 44 of the hemorrhoid and surrounding tissue. In accordance with a first embodiment, the compression portions are adapted to produce necrosis of the tissue, in the case wherein the use of the knife 26 is not foreseen.

In accordance with a second embodiment, the complementary elements 30, 32 are mutually hinged and kept closed by means of at least one elastic element 46, preferably arranged at the hinge 48. During insertion, the complementary elements 30, 32 are kept open by means of the jaws of the head.

Also in this case, mutual compression portions 44 are also foreseen serving as snap-clasping portions in order to close on the hemorrhoid and on the surrounding tissue.

Advantageously, both described and illustrated examples foresee complementary elements 30, 32 wherein at least one portion is realized in biocompatible material. Preferably, the portion in biocompatible material is arranged at the clasping or connection zone between the two complementary elements (pin or hinge in relation with the type of clip).

In accordance with an additional embodiment, the present invention relates to a device 10 for the transanal treatment of hemorrhoids comprising a handle 12, a shaft 14 which extends from the handle 12 and a head 16 arranged at the distal end of the shaft. The head 16 comprises at least one jaw 18, movable between an open position, wherein it defines a window 20 for the insertion of the hemorrhoid and surrounding tissue, and a closed position. In particular, the head is realized as previously described, i.e. it comprises a jaw 22 opposing the movable jaw. In the illustrated example, the opposing jaw is fixed and distal with respect to the movable jaw. Also in this case, it is possible to foresee that both jaws are movable or else that the position of the movable jaw and opposing jaw is reversed, foreseeing the movable jaw in distal position with respect to the opposing jaw.

According to this embodiment, the head does not foresee the presence of clipping elements. Indeed, the shaft and the head advantageously comprise means 50 for applying energy to the hemorrhoid and to the surrounding tissue in order to cut and clot the tissue. In accordance with this embodiment, the shaft may extend between the handle and the head in a curvilinear longitudinal direction. Moreover, the head, in particular the jaws, may have a curvilinear conformation.

In accordance with a first embodiment, the means for applying energy comprise ultrasound means. Alternatively, the means for applying energy comprise laser means.

According to an additional feature, the present invention relates to a method for the transanal treatment of hemorrhoids.

In general terms such method comprises the steps of:

positioning a device 10 for the transanal treatment of the hemorrhoids according to one of the previously described embodiments, locally placing the head 16 on the single hemorrhoid;

grasping and pulling the hemorrhoid through the window 20 defined by the head 16 of the device for the transanal treatment of hemorrhoids, closing the jaws 18, 22, locking the hemorrhoid and surrounding tissue, uniting the tissue portions at the zone wherein the tissue is locked between the jaws.

Moreover, the step of cutting the tissue through the jaws and removing the tissue from the site may be advantageously foreseen.

In accordance with a possible embodiment, the tissue portions are united at the zone wherein the tissue is locked between the jaws by means of at least one row of clipping elements or staples. The staples are preferably clasped to the tissue after the movement of the jaws from the open to the closed position.

In accordance with a different embodiment, the tissue portions are united at the zone wherein the tissue is locked between the jaws by means of the positioning of one clip, as previously described.

In accordance with a further embodiment, the tissue portions are united at the zone wherein the tissue is locked between the jaws by means of the application of energy, preferably ultrasound or laser, with the simultaneous cutting of the tissue.

Below, the steps of a method for the transanal treatment of hemorrhoids according the present invention are described in detail.

The patient is prepared and positioned for operation, possibly in conventional manner or according to the surgeon's preferences. A conventional preparation of the operating area is also carried out and one proceeds with the anesthesia, for example spinal or general.

A visual examination is carried out of the anal canal and perianal tissue with subsequent digital rectal examination for identifying and classifying the internal hemorrhoids and possibly examining and taking note of additional pathologies.

An anoscope is then inserted.

The internal hemorrhoid is grasped for example by means of forceps, locating an unaffected zone on the patient.

The device for the transanal treatment of hemorrhoids is then inserted and the hemorrhoid is pulled through the window of the device itself. The jaws are then closed, thus locking the hemorrhoid and surrounding tissue.

In the case wherein the device is a stapler, as previously described, preferably after closing the jaws, the clipping elements are inserted and closed through the tissue and the knife is operated to cut the hemorrhoid. The excised tissue is removed. Preferably the staples are clasped to the tissue of the anal duct in order to clot at least this portion of tissue.

In the case wherein one clip is used, as previously described, the clip is previously positioned at the open window and the tissue is pulled through the window and the open clip. The jaws' closing causes the locking of the clip on the hemorrhoid. In this case, it may be foreseen that the device also comprises a knife, and that therefore the tissue compressed by the clip is cut and removed. Alternatively, the tissue is not cut; it comes off due to the necrosis of the compressed zone. In the case of use of biocompatible material portions, the clip comes off or is absorbed once its task has been completed.

Finally, in the case of means for applying energy, after the closure of the jaws, such means (laser or ultrasound) are operated for cauterizing and cutting the tissue.

The device is then removed, possibly with the excised tissue.

Subsequently, the hemostasis is checked at the point of the cut and the anorectal junction. If the examination is satisfactory, it is possible to remove the anoscope.

Finally, a sponge is inserted in the rectum.

According to a further aspect, the present invention relates to an anoscope for the treatment of lower rectum pathologies, for example for the treatment of hemorrhoids, in particular as previously described.

An anoscope according to the present invention is indicated with 52, comprising an insertion portion 54 and an external or grip portion 56.

The insertion portion comprises a substantially tubular wall which extends from a proximal section 54a to a distal section 54b. The distal section is advantageously realized in frustoconical shape, with smaller section at the distal end of the anoscope.

Moreover, the tubular wall comprises a window 58, for example adapted to visualize the hemorrhoids and to permit the use of the above-described instruments. In particular, the window 58 involves a central section 54c and the distal section 54b of the insertion portion, opening on the distal end of the anoscope. Advantageously, the window 58 does not extend to the proximal section 54a of the insertion portion. In other words, the proximal section 54a extends with continuity in the circumferential direction, over 360°, in order to protect the anorectal junction during the procedure.

In accordance with a possible embodiment, the window 58 has a curvilinear edge, at least in the central section 54c of the insertion portion, and it widens slightly moving from the proximal to the distal section of the anoscope, at least until the beginning of the distal section.

Advantageously, in accordance with a possible embodiment, the insertion portion has a variable diameter from the proximal to the distal section, at least until the beginning of the distal section. In particular, a transverse size d2 (diameter) measured at the beginning of the proximal section is smaller than a transverse size d1 (diameter) measured at the beginning of the distal section (the term "beginning" was used in reference to moving from the proximal to the distal section of the anoscope).

The passage from the size d1 to the size d2 may be obtained by means of a curvilinear profile or more preferably a linear profile.

Preferably, the anoscope is realized in transparent material, so to have the anorectal junction constantly under observation.

Regarding the grip portion 56, at least two flanges 60 are advantageously foreseen which extend transversely with respect to the longitudinal extension of the insertion portion, so to permit the manipulation and possibly the rotation of the anoscope around the circumference of the anal/rectal wall. Advantageously, two diametrically opposed and slightly offset flanges are foreseen on one side of the anoscope.

The size of the anoscope, and in particular the size of the insertion portion, is such to permit the use of instruments such as those described above, and to avoid damaging the sphincter muscles.

With reference to the use of an anoscope, and in particular the above-described anoscope, the aforesaid method for the transanal treatment of hemorrhoids in particular foresees the steps of:

preparing the patient and the operating area;

proceeding to the anesthesia, for example spinal or general;

carrying out a visual examination of the anal canal and perianal tissue with subsequent digital rectal examination for identifying and classifying the internal hemorrhoids;

inserting an anoscope, in particular an anoscope as previously described;

positioning the window 58 at the hemorrhoid and grasping the hemorrhoid through the window by inserting grasping means 62 through the anoscope and window;

preferably locating an unaffected zone on the patient;

inserting inside the anoscope a device for the transanal treatment of hemorrhoids, in particular as previously described, making the head 16 project through the window 58;

pulling the hemorrhoid through the anoscope window and through the device window;

closing the jaws, thus locking the hemorrhoid and surrounding tissue.

In the case wherein the device is a stapler, as previously described, the clipping elements or staples are inserted and closed through the tissue and the knife is operated to cut the hemorrhoid preferably after the movement of the head from the open to the closed position. The excised tissue is removed by extracting it from the anoscope.

In the case wherein one clip is used, as previously described, the clip is previously positioned at the open window and the tissue is pulled through the anoscope window, device window and through the open clip. The jaws' closing causes the locking of the clip on the hemorrhoid. In this case, it may be foreseen that the device also comprises a knife, and that therefore the tissue compressed by the clip is cut and removed through the anoscope. Alternatively, the tissue is not cut; it comes off due to the necrosis of the compressed zone. In the case of use of biocompatible material portions, the clip comes off or is absorbed once its task has been completed.

Finally, in the case of means for applying energy, after the closure of the jaws, such means (laser or ultrasound) are operated for cauterizing and cutting the tissue.

The device is then removed, possibly with the excised tissue, and the anoscope is also subsequently removed. Possible, a sponge is inserted in the rectum.

From the above, it may be appreciated how foreseeing a method according to the present invention permits obtaining a more radical result, without producing a large wound over the entire circumference of the anal canal.

The device, clip and anoscope described above permit simplifying procedures, reducing the patient risks. Moreover, they permit the elimination of every single hemorrhoid, possibly operating in several subsequent steps in order to avoid creating excessive discomfort for the patient.

The stapling line or the clip is adapted to be correctly positioned. By means of the hemorrhoid traction, they may be moreover more deeply positioned with respect to the use of the elastic band. Moreover, their position is ensured, is stable over the course of the procedure or post-operative course.

Clearly, variations and/or additions to that described and illustrated above may be foreseen.

For example, the aforesaid device may extend in a curvilinear longitudinal direction comprising one or more curved portions.

Regarding the preferred embodiment of the device, clip, method or anoscope described above in relation with the treatment of hemorrhoids, but suitable in general for a intraluminal treatment of body tissue, e.g. also for the treatment of body tissue different from hemorrhoids, a person skilled in the art, in order to satisfy contingent and specific needs, may produce numerous modifications, adaptations and substitutions of elements with other functionally equivalent elements without however leaving the scope of the following claims.

The invention claimed is:

1. Method for the intraluminal transanal treatment of body tissuelower rectum pathologies comprising the steps of:
    providing a device having a handle, a head and a curvilinear shaft longitudinally extended between the handle and the head, said head comprising two curvilinear jaws, movable between an open position, in which said jaws open a window laterally to the longitudinally shaft extension, and a closed position,
    providing an anoscope comprising an insertion portion and a grip portion, wherein the insertion portion comprises a substantially tubular wall having a tubular proximal section extending distally from said grip portion, a truncated cone shaped distal section and a central section extending between the proximal section and the distal section, and a window opening formed in said central section and distal section and opening on a distal end of the anoscope,
    transanally inserting the anoscope and positioning the window opening of the anoscope at a body tissue, grasping the tissue through the window opening,
    inserting the device inside the anoscope and placing the head of the device through the window opening of the anoscope at the tissue to be treated, locally placing the head on the single tissue;
    grasping and pulling the tissue through the window opening of the anoscope and through the window defined by the head of the device,
    closing the jaws, locking the tissue and surrounding tissue portions,
    uniting the surrounding tissue portions at the zone wherein the tissue is locked between the jaws.

2. Method according to claim 1, moreover comprising the step of cutting the tissue through the jaws and removing it from the site.

3. Method according to claim 1, wherein the surrounding tissue portions are joined at the zone wherein the tissue is locked between the jaws by means of at least one row of clipping elements or staples.

4. Method according to claim 3, wherein the staples are clasped to the tissue to be treated after the head movement from an open position to a closed position.

5. Method according to claim 4, wherein the tissue is cut through the jaws when the staples are clasped to the tissue to be treated.

6. Method according to claim 1, wherein the surrounding tissue portions are united at the zone wherein the tissue is locked between the jaws by means of positioning tightening only one clip on the tissue, a clip
    comprising two curvilinear complementary elements received in the head of the device and mutually locked by said device in at least one compression position around the tissue to be treated and surrounding tissue.

7. Method according to claim 1, wherein the surrounding tissue portions are united at the zone wherein the tissue is locked between the jaws by means of applying ultrasound causing energy, preferably ultrasound or laser, with the simultaneous cutting and clotting of the tissue.

* * * * *